(12) United States Patent
Chirnside

(10) Patent No.: US 6,342,222 B1
(45) Date of Patent: ***Jan. 29, 2002

(54) EQUINE ARTERITIS VIRUS PEPTIDES, ANTIBODIES AND THEIR USE IN A DIAGNOSTIC TEST

(75) Inventor: Ewan D Chirnside, Newmarket (GB)

(73) Assignee: The Minister of Agriculture, Fisheries and Food in Her Britannic Majesty's Government of the United Kingdom of Great Britain and Northern Ireland

( * ) Notice: Subject to any disclaimer, the term of this patent is extended or adjusted under 35 U.S.C. 154(b) by 0 days.

This patent is subject to a terminal disclaimer.

(21) Appl. No.: 09/063,431

(22) Filed: Apr. 21, 1998

Related U.S. Application Data

(62) Division of application No. 08/676,169, filed as application No. PCT/GB95/00066 on Jul. 31, 1996, now Pat. No. 5,773,235.

(30) Foreign Application Priority Data

Jan. 14, 1994 (GB) .............................................. 9400656

(51) Int. Cl.[7] ........................ A61K 39/12; C07H 21/04; C07K 14/18; C12N 7/00

(52) U.S. Cl. .................... 424/186.1; 435/7.92; 435/7.1; 435/69.1; 530/300; 536/23.72; 424/184.1; 424/185.1; 424/193.1; 424/218.1

(58) Field of Search ................................. 435/7.92, 7.1, 435/69.1; 530/388.3, 389.4, 300; 536/23.72; 424/186.1, 184.1, 185.1, 193.1, 218.1; 436/536

(56) References Cited

PUBLICATIONS

Lederman et al. Molecular Immunology, vol. 28, No. 11 p. 1171–1181, 1991.*
de Vries et al. J Virol., Nov. 1992, 66(11), pp. 6294–6303.*
Deregt et al. J Gen Virol. Sep. 1994, 75(Pt. 9), pp. 2439–2444.*
Balasuriya et al J. Gen. Virol vol. 74, 1993 pp. 2525–2529.
Boon et al J. Virol. vol. 65, No. 6, Jun. 1991, pp. 2910–2920.

* cited by examiner

*Primary Examiner*—Phuong T. Bui
(74) *Attorney, Agent, or Firm*—Nixon & Vanderhye P.C.

(57) ABSTRACT

A peptide or peptide conjugate is provided comprising one or more epitopes capable of producing an immune response against equine arteritis virus in animals. The peptides and conjugates are useful in vaccines directed against equine arteritis virus, an agent implicated in equine abortion, and as binding agents for use in binding assays, including ELISA assays, for antibodies thereto. Antibodies and antisera to the peptides and peptide conjugates may also be used as such binding agents in assays directed at the virus itself.

4 Claims, 2 Drawing Sheets

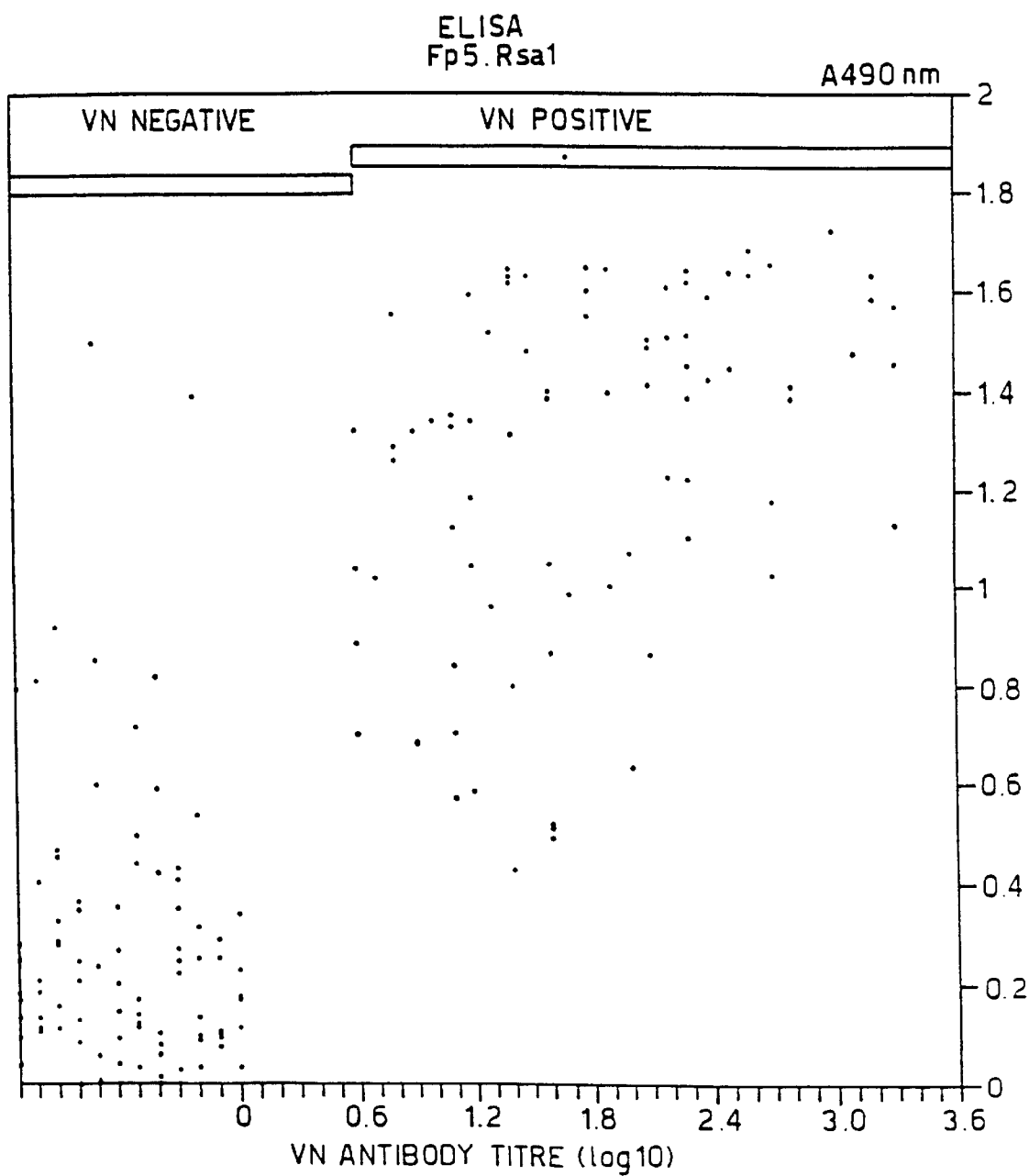

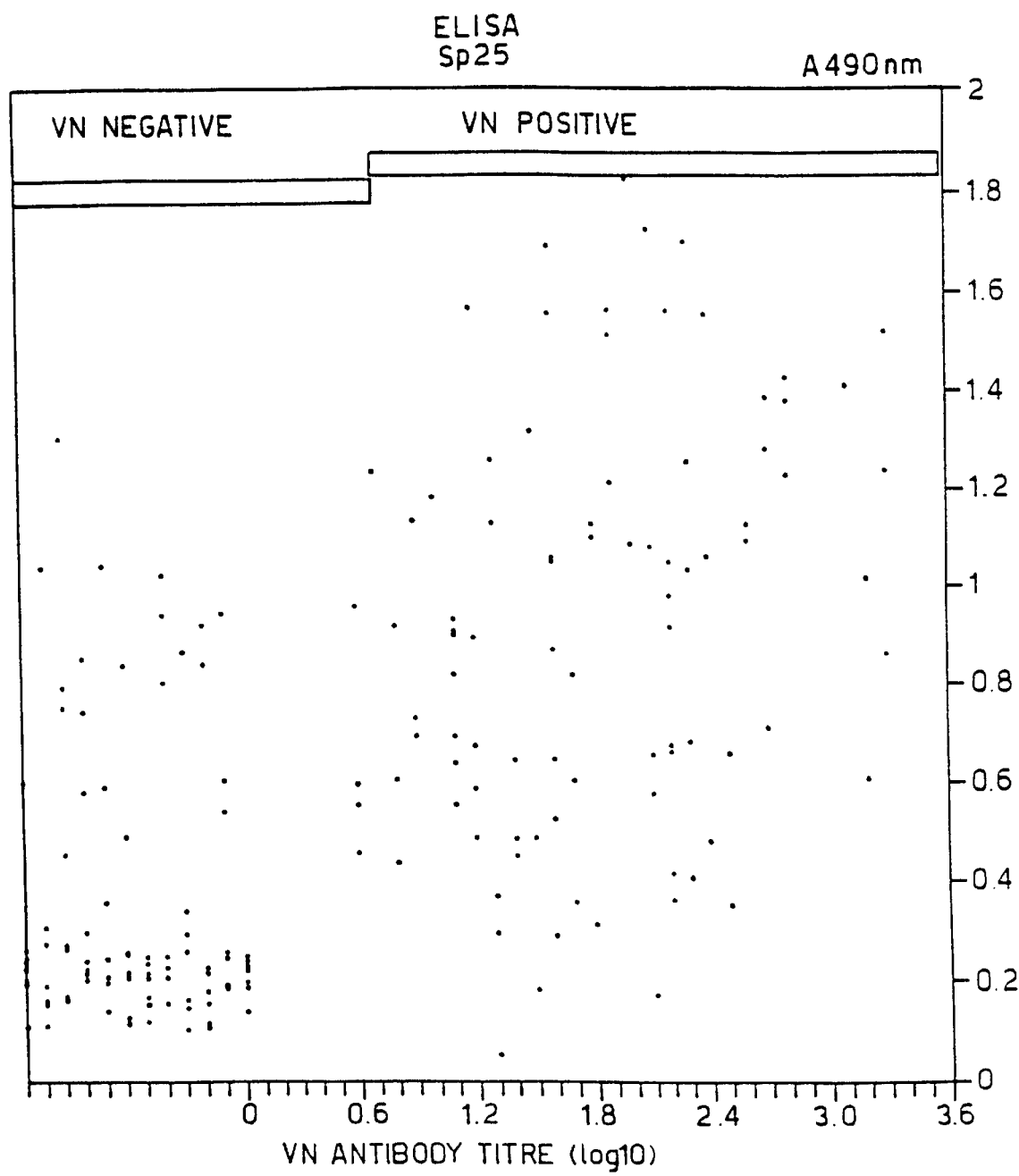

EQUINE ARTERITIS VIRUS PEPTIDES, ANTIBODIES AND THEIR USE IN A DIAGNOSTIC TEST

This is a division of application Ser. No. 08/676,169, filed Jul. 31, 1996, now U.S. Pat. No. 5,773,235.

The present invention relates to recombinant DNA and proteins encoded thereby having use in provision of vaccines, diagnostics test kits and methods of diagnosis for equine arteritis virus (EAV) and equine arteritis virus mediated disease.

Equine viral arteritis, a disease for which horses and donkeys are the only reported hosts, has been known for some 40 years and manifests itself with widely varying clinical signs. In its most severe form EAV infection causes abortion which makes it a potentially significant commercial threat to, inter alia, the race horse breeding industry. Early veterinary articles refer to it as epizootic cellulitus pinkeye or equine influenza. Disease outbreaks are identified infrequently and field isolates of the single stranded RNA virus itself are rare.

The virus is transmitted by the respiratory and venereal routes, with a 30% carrier state existing in seropositive stallions making the latter route a particular cause for concern as these shedding stallions may consequently infect brood-mares. In the light of the potential economic importance of the virus and its stud carrier mediated infection capability there exist a requirement for both prophylactic treatment and reliable diagnosis of EAV.

Laboratory tests based upon ELISA, virus neutralisation (VN) and complement fixation (CF) formats have been developed (see Chirnside (1992) Br. vet. J. 148 pp181). The known ELISA is relatively insensitive when applied to tissues, eg. sera, from horses previously vaccinated for other diseases such as influenza and herpesvirus, while the VN and CF formats have limited temporal sensitivity; the VN test is unable to distinguish between vaccination and natural infection.

Vaccination procedures have concentrated on safety and efficacy of whole inactivated virus and attenuated live virus vaccine. The live vaccine can induce shedding of virus from the nasopharynx and does not prevent this causing infection of commonly housed animals that have not been so treated. The known formalinised vaccine does not provide reliable protection.

Attempts to provide improvements to both diagnostic tests and vaccines have included studies into panels of antibodies raised against various EAV proteins. A 29K envelope protein in particular has been identified as antigenic and capable of causing production of neutralising antibodies in mouse (Balasuriya et al (1993) Journal of General Virology, 74, p2525–2529). The identity of this protein is unknown but work reported since the priority date of the present application by Deregt et al (J. General Virology 75, pp2439–2444) has shown that some monoclonal antibodies raised to $G_L$ protein are EAV neutralising, as are those to the nucleocapsid N protein. Results of tests in horse have yet to be reported.

The present inventor now provides isolated peptides that produce a potent neutralising immune response against EAV when administered to animals, particularly horses, and these peptides provide sensitive detection of EAV antibodies when used as binding agent in binding assay format. Further provided is DNA encoding for these peptides.

In a first aspect of the present invention there is provided a peptide or peptide conjugate comprising one or more epitopes capable of evoking an immune response in animals producing antibodies which are neutralising to equine arteritis virus, characterised in that the epitopes are selected from those present in the amino acid sequence corresponding to amino acid 19 to 137 (SEQ ID No 3) of equine arteritis virus (EAV) $G_L$ protein; the peptide not being the $G_L$ protein.

Preferred peptides or peptide conjugates of the invention comprise the epitopes present in the amino acid sequence corresponding to amino acid 28 to 137 (SEQ ID No 4), more preferably 75 to 97 (SEQ ID No 5) and most preferably 85 to 97 (SEQ ID No 7) of EAV $G_L$. Preferred peptides or peptide conjugates comprise the amino acid sequence corresponding to amino acid 75 to 97 or a sequence having at least 90% homology thereto; preferably comprising an amino acid sequence corresponding to a sequence at least 90% homologous to the sequence of amino acids 28 to 137 of equine arteritis virus $G_L$ protein (SEQ ID No 4), but including said 85 to 97, or more preferably the 75 to 97 sequence, or a sequence that has at least 90% homology thereto. Other desirable optional epitopes identified are at 33 to 44 and 53 to 64.

A second aspect of the present invention provides a peptide or peptide conjugate comprising one or more epitopes capable of evoking an immune response in animals that produces antibodies which are neutralising to equine arteritis virus, characterised in that the epitopes are selected from those present in the amino acid sequence corresponding to amino acid 19 to 137 of equine arteritis virus $G_L$ protein (SEQ ID No 3), for use as a diagnostic agent; such peptide or conjugate is particularly provided for use as a diagnostic agent for the detection of EAV. Such aspect of course includes equine arteritis virus $G_L$ protein as such for these uses. Peptides or conjugates comprising SEQ ID No 2 are preferred; $G_L$ protein being included for such use; but peptides or conjugates comprising an amino acid sequence corresponding to a sequence at least 90% homologous to the sequence of amino acids 19 to 137 of equine arteritis $G_L$ protein (SEQ ID No 3) or to SEQ ID No 4, while retaining the amino acids 75 to 97 (SEQ ID No 5 and most preferably retaining the amino acids 85 to 97 (SEQ ID No 7) of, or having at least 90% homology to, SEQ ID No 2 may be used.

In a third aspect of the present invention are provided compositions comprising isolated peptides or peptide conjugates as described above per se, including $G_L$, particularly for use in evoking neutralising antibody responses, eg. for the purpose of prophylaxis or diagnosis. Typically such compositions will comprise a peptide or conjugate of the present invention together with a pharmaceutically acceptable carrier or a carrier suitable for use in binding studies respectively.

In a fourth aspect of the present invention there is provided recombinant DNA, or RNA derived therefrom, encoding for peptides or conjugates of the invention, and plasmids and cells transformed thereby comprising this DNA such that they are capable of expressing the peptides or conjugates. This DNA has sequences of SEQ ID Nos 3 to 7 and those indicated in Table 1 below, and may be incorporated into cells in the form of vectors such as plasmids or may be used as a 'naked vaccine' by way of chromosomal integration; both techniques being well understood by those skilled in the art.

In a fifth aspect of the present invention there is provided a method for testing for the presence of antibodies to equine arteritis virus comprising use of a peptide or peptide conjugate of the present invention, or $G_L$ protein, as a specific binding agent. Such test is preferably of ELISA format but may use the peptide or conjugate as immobilised binding agent or labelled secondary binding agent in a so called sandwich assay.

In binding assay where the peptide or peptide conjugate is immobilised this method may conveniently be carried out by use of commercially available assay plates onto which the peptide or conjugate is coated by suitable incubation in the known manner. For the purpose of assay a sample to be screened for EAV antibodies, eg. a serum sample, is typically incubated in contact with the plate, eg. in the wells, whereafter any EAV antibody present therein is identified by exposure to eg. an anti-horse IgA, IgG or IgM conjugated to a reporter group. Such reporter group may be in the form of a radiolabel, chemical label or a biological label. A typical biological label is an enzyme or cofactor, eg. biotin, and is detected by exposure to all the reactants necessary for a reporter reaction to occur dependent upon the presence of the reporter group. In the case of biotin the well may be exposed to streptavidin-peroxidase and then o-phenylenediamine dihydrochloride and the absorbance of the plate determined at 490 nm.

In a further example an immobilised anti-horse IgA, IgM or IgG antibody raised in another animal may be used to bind a specific class of horse antibody and then the immobilised horse antibody provided may be exposed to a solution containing labelled peptide or conjugate of the invention whereby presence of anti-EAV antibody is indicated by assay of the amount of label present. Other assay formats such as competitive assays using either bound and unbound peptide or conjugate will occur to those skilled in the art; these will include simple observation of agglutination between peptide or conjugate and the antibody in a simple dilution test.

In a further aspect of the present invention there are provided test kits for use in carrying out the assay of the invention characterised in that they comprise a peptide, peptide-conjugate or antibodies of the invention, together with optional agents and items necessary for performing such assays. Such agents and items may include other binding agents or colour forming agents such as labelled antibodies, eg. biotinylated anti-horse IgG, horseradish peroxidase, streptavidin-peroxidase conjugate and o-phenylenediamine dihydrochloride. It will be realised that the term peptide and peptide conjugate as used herein will encompass oligopeptides, polypeptides and proteins as long as they fulfil the criteria of the invention with regard to immunological activity and content of epitopic sequences. The term 'conjugate' designates conjugation to any physiologically acceptable entity.

The peptides, peptide conjugates and binding assays of the present invention will now be described by way of example only by reference to the following sequence listing, figures and examples.

Sequence Listing

SEQ ID No 1: is the DNA sequence equivalent to the entire EAV genome minus the first 18 bases and the polyA tail.

SEQ ID No 2: is the amino acid sequence corresponding to amino acids 1 to 137 of the EAV $G_L$ protein (including any signal sequence).

SEQ ID No 3: is the amino acid sequence corresponding to amino acids 19 to 137 of the EAV $G_L$ protein.

SEQ ID No 4: is the amino acid sequence corresponding to amino acids 28 to 137 of the EAV $G_L$ protein.

SEQ ID No 5: is the amino acid sequence corresponding to amino acids 75 to 97 of the EAV $G_L$ protein.

SEQ ID No 6: is the amino acid sequence that is fused with GST in Fp5.RsaI and used in the ELISA of Example 3.

SEQ ID No 7: is the amino acid sequence corresponding to the epitope at $G_L$ 85 to 97.

FIGURES

FIG. 1: shows a graph relating $A_{490}$ values obtained using an Fp5.RsaI fusion protein ELISA carried out as described in Example 3 with VN derived results on the samples from the same horses.

FIG. 2: shows a graph relating $A_{490}$ values obtained using an Sp25 ELISA carried out as described in Example 3 with VN derived results on samples from the same horses.

EXAMPLE 1

Production of Peptides and Conjugates of the Invention and DNA and Vectors Encoding Therefor cDNA encompassing EAV open reading frames (ORFs) 2 to 7 (as referred to by De Vries et al, 1992) corresponding to EAV proteins $G_s$, 3, 4, $G_L$, M and N were cloned into the bacterial expression vectors pGEX-3X and pGEX-2T (Table 1) and constructs screened for fusion protein expression using PAGE with cloning confirmed by RE digestion analysis and sequencing over the plasmid/insert junctions. Affinity purified gluthathione-S-transferase (GST) fusion proteins were screened for reactivity by indirect ELISA with a panel of virus neutralising equine sera. Of the six fusion proteins (Fp2.0–Fp7.0) screened by this ELISA only Fp5.0 (see SEQ ID No 2 for EAV peptide content), corresponding to amino acids 28–137 of EAV $G_L$ plus GST reacted strongly with the neutralising sera. A panel of 96 neutralising and 96 non-neutralising sera were then tested by indirect ELISA against Fp5.0. Amongst the virus neutralising sera tested 96/96 produced an $A_{490}$ greater than 0.4 against Fp5.0 in the ELISA with absorbance readings exhibiting a linear correlation to virus neutralising antibody titres (FIG. 1). 12/96 of the neutralising equine sera tested positive to Fp5.0 in this ELISA.

Additional cloning experiments were performed with ORF 5 to produce fusion products 5.1, 5.2 and 5.4 which were affinity purified prior to testing with ELISA. Although Fp5.2 from this series of constructs was overexpressed during culture it proved difficult to affinity purify so a further round of cloning was performed to produce Fp5.RsaI.

TABLE 1

EAV expression clone data:

| ORF | Fp | Vector pGEX Digest | SEQ ID No 1 | EAV Digest |
|---|---|---|---|---|
| 2 | 2.0 | 2T xSmaI*EcoRI | 10007–11476 | BalI-EcoRI |
| 3 | 3.0 | 3X xSmaI | 10310–10708 | HaeIII |
| 4 | 4.0 | 3X xBamHI*EcoRI | 10688–11205 | BglII-EcoRI$^V$ |
| 5 | 5.0 | 3X xSmaI | 11210–11538 | HaeII$^B$-ScaI |
| 6 | 6.0 | 3X xEcoRI$^B$ | 11897–12380 | HinfI$^B$-FspI |
| 7 | 7.0 | 3X xSmaI | 12287–12687 | HindIII$^V$ |
| 5 | 5.1 | 3X xSmaI | 11114–11291 | RsaI |
| 5 | 5.2 | 3X xSmaI | 11240–11475 | Sau3AI$^B$-EcoRI |
| 5 | 5.4 | 3X xEcoRI$^B$ | 11739–11876 | PvuII |
| 5 | 5.RsaI | 3X xEcoRI$^B$ | 11292–11423 | RsaI |

$^V$= vector derived RE digestion site
$^B$= fragment/vector made blunt ended with Klenow DNA polymerase and T4 polymerase.

Peptide Sp25 (SEQ ID No 5) was also directly synthesised corresponding to the amino acid sequence of equine arteritis virus $G_L$ protein amino acid 75 to 97 and this and the product of Fp5.RSaI were tested with the ELISA as described in Example 3 (see FIGS. 1 and 2). Fp5.RsaI was subsequently used in ELISA tests during the UK EAV outbreak in June 1993 to rapidly screen sera (Table 2) and used to test 1264 equine sera from a serosurvey carried out on Italian stallions (Table 3).

EXAMPLE 2
Immunisation Studies

Fp5.0, Fp5.RsaI and Sp25 were used to immunise rabbits and proved capable of inducing neutralising antibody response. Subsequent immunisation conducted on three groups of three horses confirmed Sp25 and Fp5.RsaI induce neutralising antibodies at a dose of 60 μg of EAV-specific peptide/conjugate agent for both groups. The peptide was delivered as an agent consisting of Sp25 coupled to keyhole limpet haemocyanin (KLH) and all vaccine doses were adjuvanted with Duphar polymer adjuvant at 0.5%. Doses were given at 0.51 and 114 days; Sp25 and RsaI giving strong antibody production after each dose.

EXAMPLE 3
ELISA using Fp5.RsaI or Sp25 as Binding Agent

Dynatech Immulon 3 microtitre plate wells were coated with Fp5.RsaI or Sp25 antigen by exposure to 100 μl of 5 μg/ml antigen in 0.05M carbonate buffer at pH9.6 (Sigma cat No C3041) at 4° C. overnight.

Plates were washed three times with Phosphate Buffered Saline (PBS) containing 0.05% Tween 20 (thereafter PBST) and then blocked with 100 μl PSBT containing 5% normal goat serum (Seralab) (thereafter PBSTG) for 1 hour at 37° C. Plates were washed again three times with PBST to render them ready for use.

Test sera were diluted 1:100 in PBSTG and 100 μl of this solution added to wells prepared as above and incubated for 90 minutes at 37° C. Plates were washed again three times with PBST and solution prepared by diluting 100 μl goat anti-horse IgG biotin conjugate (KPL catalog No 162102) 1:1000 in PBSTG and adding to each well before being incubated for 90 minutes at 37° C. Plates were washed three times with PSBT and a solution prepared by diluting 100 μl streptavidin-peroxidase conjugate (KPL catalog No 14-30-00) 1:1000 in PBSTG and adding to each well before incubating at room temperature for 30 minutes. Plates were washed three times with PBST and 100 μl o-phenylenediamine dihydro-chloride (Sigma cat No. P8287) (0.5 mg/ml in 0.05 phosphate citrate buffer, pH5.0-Sigma cat No. P4922) added to each well and incubated for 10 minutes at room temperature. 50 μl 4M $H_2SO_4$ was added to stop the reaction and absorbance was read at 490 nm. Since horse sera at a 1:100 dilution can bind native GST it is necessary to subtract absorbance readings obtained for sera against GST from GST-fusion protein absorbance. Each serum sample is tested in duplicate wells against each antigen. In each ELISA test 8 EAV VN positive sera and 8 EAV VN negative sera were run as internal controls.

TABLE 2

EAV outbreak 1993-Fp5.RsaI ELISA vs VN results.

| | | |
|---|---|---|
| ELISA positive VN negative | 46 | (on 32 animals) |
| ELISA negative VN positive | 1 | |
| ELISA positive VN positive | 148 | |
| ELISA negative VN negative | 374 | |
| ELISA and VN detected 17 animals that were seroconverters | | |

TABLE 3

Italian stallions 1993-Fp5.RsaI vs VN results

| | |
|---|---|
| ELISA positive VN negative | 369 |
| ELISA negative VN positive | 21 |
| ELISA positive VN positive | 441 |
| ELISA negative VN negative | 433 |

Samples assigned as ELISA positive if $A_{490}$ is over 0.15 16/21 of the ELISA negative VN positives had VN titres below 1/16

What is claimed is:

1. A peptide of the equine arteritis virus $G_L$ protein which elicits an immune response in animals to whom the peptide is administered and results in the production of neutralizing antibodies against equine arteritis virus, said peptide consisting of an oligopeptide having between 13 and 119 amino acids, and wherein said peptide comprises a region of an equine arteritis virus $G_L$ protein and said region includes SEQ ID NO:7.

2. A peptide conjugate which elicits an immune response in animals to whom the peptide conjugate is administered and results in the production of neutralizing antibodies against equine arteritis virus, wherein the peptide conjugate consists of a peptide as claimed in claim 1, conjugated to a further heterologous peptide, protein or other physiologically acceptable molecule.

3. A diagnostic agent for the detection of equine arteritis virus, said agent comprising a peptide conjugate according to claim 2.

4. A diagnostic agent for the detection of equine arteritis virus, said agent comprising a peptide according to claim 1.

* * * * *

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 12687 base pairs
      (B) TYPE: nucleic acid
      (C) STRANDEDNESS: single
      (D) TOPOLOGY: unknown (ii) MOLECULE TYPE: cDNA (xi) SEQUENCE DESCRIPTION: SEQ ID NO: 1:

```
TGCCATATAC GGCTCACCAC CATATACACT GCAAGAATTA CTATTCTTGT GGGCCCCTCT      60

CGGTAAATCC TAGAGGGCTT TCCTCTCGTT ATTGCGAGAT TCGTCGTTAG ATAACGGCAA     120

GTTCCCTTTC TTACTATCCT ATTTTCATCT TGTGGCTTGA CGGGTCACTG CCATCGTCGT     180

CGATCTCTAT CAACTACCCT TGCGACTATG GCAACCTTCT CCGCTACTGG ATTTGGAGGG     240

AGTTTTGTTA GGGACTGGTC CCTGGACTTA CCCGACGCTT GTGAGCATGG CGCGGGATTG     300

TGCTGCGAAG TGGACGGCTC CACCTTATGC GCCGAGTGTT TTCGCGGTTG CGAAGGAATG     360
```

-continued

```
GAGCAATGTC CTGGCTTGTT CATGGGACTG TTAAAACTGG CTTCGCCAGT TCCAGTGGGA      420

CATAAGTTCC TGATTGGTTG GTATCGAGCT GCCAAAGTCA CCGGGCGTTA CAATTTCCTT      480

GAGCTGTTGC AACACCCTGC TTTCGCCCAG CTGCGTGTGG TTGATGCTAG GTTAGCCATT      540

GAAGAGGCAA GTGTGTTTAT TTCCACTGAC CACGCGTCTG CTAAGCGTTT CCCTGGCGCT      600

AGATTTGCGC TGACACCGGT GTATGCTAAC GCTTGGGTTG TGAGCCCGGC TGCTAACAGT      660

TTGATAGTGA CCACTGACCA GGAACAAGAT GGGTTCTGCT GGTTAAAACT TTTGCCACCT      720

GACCGCCGTG AGGCTGGTTT GCGGTTGTAT TACAACCATT ACCGCGAACA AAGGACCGGG      780

TGGCTGTCTA AAACAGGACT TCGCTTATGG CTTGGAGACC TGGGTTTGGG CATCAATGCG      840

AGCTCTGGAG GGCTGAAATT CCACATTATG AGGGGTTCGC CTCAGCGAGC TTGGCATATC      900

ACAACACGCA GCTGCAAGCT GAAGAGCTAC TACGTTGTG ACATCTCTGA AGCAGACTGG      960

TCCTGTTTGC CTGCTGGCAA CTACGGCGGC TACAATCCAC CAGGGGACGG AGCTTGCGGT     1020

TACAGGTGCT TGGCCTTCAT GAATGGCGCC ACTGTTGTGT CGGCTGGTTG CAGTTCTGAC     1080

TTGTGGTGTG ATGATGAGTT GGCTTATCGA GTCTTTCAAT TGTCACCCAC GTTCACGGTT     1140

ACCATCCCAG GTGGGCGAGT TTGTCCGAAT GCCAAGTACG CAATGATTTG TGACAAGCAG     1200

CACTGGCGCG TCAAACGTGC AAAGGGCGTC GGCCTGTGTC TCGATGAAAG CTGTTTCAGG     1260

GGCATCTGCA ATTGCCAACG CATGAGTGGA CCACCACCTG CACCCGTGTC AGCCGCCGTG     1320

TTAGATCACA TACTGGAGGC GGCGACGTTT GGCAACGTTC GCGTGGTTAC ACCTGAAGGG     1380

CAGCCACGCC CCGTACCAGC GCCGCGAGTT CGTCCCAGCG CCAACTCTTC TGGAGATGTC     1440

AAAGATCCGG CGCCCGTTCC GCCAGTACCA AAACCAAGGA CCAAGCTTGC CACACCGAAC     1500

CCAACTCAGG CGCCCATCCC AGCACCGCGC ACGCGACTTC AAGGGGCCTC AACACAGGAG     1560

CCACTGGCGA GTGCAGGAGT TGCTTCTGAC TCGGCACCTA AATGGCGTGT GGCCAAAACT     1620

GTGTACAGCT CCGCGGAGCG CTTTCGGACC GAACTGGTAC AACGTGCTCG GTCCGTTGGG     1680

GACGTTCTTG TTCAAGCGCT ACCGCTCAAA ACCCCAGCAG TGCAGCGGTA TACCATGACT     1740

CTGAAGATGA TGCGTTCACG CTTCAGTTGG CACTGCGACG TGTGGTACCC TTTGGCTGTA     1800

ATCGCTTGTT TGCTCCCTAT ATGGCCATCT CTTGCTTTGC TCCTTAGCTT TGCCATTGGG     1860

TTGATACCCA GTGTGGGCAA TAATGTTGTT CTGACAGCGC TTCTGGTTTC ATCAGCTAAT     1920

TATGTTGCGT CAATGGACCA TCAATGTGAA GGTGCGGCTT GCTTAGCCTT GCTGGAAGAA     1980

GAACACTATT ATAGAGCGGT CCGTTGGCGC CCGATTACAG GCGCGCTGTC GCTTGTGCTC     2040

AATTTACTGG GGCAGGTAGG CTATGTAGCT CGTTCCACCT TTGATGCAGC TTATGTTCCT     2100

TGCACTGTGT TCGATCTTTG CAGCTTTGCT ATTCTGTACC TCTGCCGCAA TCGTTGCTGG     2160

AGATGCTTCG GACGCTGTGT GCGAGTTGGG CCTGCCACGC ATGTTTTGGG CTCCACCGGG     2220

CAACGAGTTT CCAAACTGGC GCTCATTGAT TTGTGTGACC ACTTTTCAAA GCCCACCATC     2280

GATGTTGTGG GCATGGCAAC TGGTTGGAGC GGATGTTACA CAGGAACCGC CGCAATGGAG     2340

CGTCAGTGTG CCTCTACGGT GGACCCTCAC TCGTTCGACC AGAAGAAGGC AGGAGCGACT     2400

GTTTACCTCA CCCCCCCTGT CAACAGCGGG TCAGCGCTGC AGTGCCTCAA TGTCATGTGG     2460

AAGCGACCAA TTGGGTCCAC TGTCCTTGGG AACAAACAG GAGCTGTTGT GACGGCGGTC      2520

AAGAGTATCT CTTTCTCACC TCCCTGCTGC GTCTCTACCA CTTTGCCCAC CCGACCCGGT     2580

GTGACCGTTG TCGACCATGC TCTTTACAAC CGGTTGACTG CTTCAGGGGT CGATCCCGCT     2640

TTATTGCGTG TTGGGCAAGG TGATTTTCTA AAACTTAATC CGGGGTTCCG GCTGATAGGT     2700

GGATGGATTT ATGGGATATG CTATTTTGTG TTGGTGGTTG TGTCAACTTT TACCTGCTTA     2760
```

-continued

```
CCTATCAAAT GTGGCATTGG CACCCGCGAC CCTTTCTGCC GCAGAGTGTT TTCTGTACCC    2820
GTCACCAAGA CCCAAGAGCA CTGCCATGCT GGAATGTGTG CTAGCGCTGA AGGCATCTCT    2880
CTGGACTCTC TGGGGTTAAC TCAGTTACAA AGTTACTGGA TCGCAGCCGT CACTAGCGGA    2940
TTAGTGATCT TGTTGGTCTG CCACCGCCTG GCCATCAGCG CCTTGGACTT GTTGACTCTA    3000
GCTTCCCCTT TAGTGTTGCT TGTGTTCCCT TGGGCATCTG TGGGGCTTTT ACTTGCTTGC    3060
AGTCTCGCTG GTGCTGCTGT GAAAATACAG TTGTTGGCGA CGCTTTTTGT GAATCTGTTC    3120
TTTCCCCAAG CTACCCTTGT CACTATGGGA TACTGGGCGT GCGTGGCGGC TTTGGCCGTT    3180
TACAGTTTGA TGGGCTTGCG AGTGAAAGTG AATGTGCCCA TGTGTGTGAC ACCTGCCCAT    3240
TTTCTGCTGC TGGCGAGGTC AGCTGGACAG TCAAGAGAGC AGATGCTCCG GGTCAGCGCT    3300
GCTGCCCCCA CCAATTCACT GCTTGGAGTG GCTCGTGATT GTTATGTCAC AGGCACAACT    3360
CGGCTGTACA TACCCAAGGA AGGCGGGATG GTGTTTGAAG GCTATTCAG GTCACCGAAG     3420
GCGCGCGGCA ACGTCGGCTT CGTGGCTGGT AGCAGCTACG GCACAGGGTC AGTGTGGACC    3480
AGGAACAACG AGGTCGTCGT ACTGACAGCG TCACACGTGG TTGGCCGCGC TAACATGGCC    3540
ACTCTGAAGA TCGGTGACGC AATGCTGACT CTGACTTTCA AAAAGAATGG CGACTTCGCC    3600
GAGGCAGTGA CGACACAGTC CGAGCTCCCA GGCAATTGGC CACAGTTGCA TTTCGCCCAA    3660
CCAACAACCG GCCCGCTTC ATGGTGCACT GCCACAGGAG ATGAAGAAGG CTTGCTCAGT     3720
GGCGAGGTTT GTCTGGCGTG GACTACTAGT GGCGACTCTG GATCTGCAGT GGTTCAGGGT    3780
GACGCTGTGG TAGGGGTCCA CACCGGTTCG AACACAAGTG GTGTTGCCTA CGTGACCACC    3840
CCAAGCGGAA AACTCCTTGG CGCCGACACC GTGACTTTGT CATCACTGTC AAAGCATTTC    3900
ACAGGCCCTT TGACATCAAT CCCGAAGGAC ATCCCTGACA ACATTATTGC CGATGTTGAT    3960
GCTGTTCCTC GTTCTCTGGC CATGCTGATT GATGGCTTAT CCAATAGAGA GAGCAGCCTT    4020
TCTGGACCTC AGTTGTTGTT AATTGCTTGT TTTATGTGGT CTTATCTTAA CCAACCTGCT    4080
TACTTGCCTT ATGTGCTGGG CTTCTTTGCC GCTAACTTCT TCCTGCCAAA AAGTGTTGGC    4140
CGCCCTGTGG TCACTGGGCT TCTATGGTTG TGCTGCCTCT TCACACCGCT TTCCATGCGC    4200
TTGTGCTTGT TCCATCTGGT CTGTGCTACC GTCACGGGAA ACGTGATATC TTTGTGGTTC    4260
TACATCACTG CCGCTGGCAC GTCTTACCTT TCTGAGATGT GGTTCGGAGG CTATCCCACC    4320
ATGTTGTTTG TGCCACGGTT CCTAGTGTAC CAGTTCCCCG GCTGGGCTAT TGGCACAGTA    4380
CTAGCGGTAT GCAGCATCAC CATGCTGGCT GCTGCCCTCG GTCACACCCT GTTACTGGAT    4440
GTGTTCTCCG CCTCAGGTCG CTTTGACAGG ACTTTCATGA TGAAATACTT CCTGGAGGGA    4500
GGAGTGAAAG AGAGTGTCAC CGCCTCAGTC ACCCGCGCTT ATGGCAAACC AATTACCCAG    4560
GAGAGTCTCA CTGCAACATT AGCTGCCCTC ACTGATGATG ACTTCCAATT CCTCTCTGAT    4620
GTGCTTGACT GTCGGGCCGT CCGATCGGCA ATGAATCTCG GTGCCGCTCT CACAAGTTTT    4680
CAAGTGGCGC AGTATCGTAA CATCCTTAAT GCATCCTTGC AAGTCGATCG TGACGCTGCT    4740
CGTAGTCGCA GACTAATGGC AAAACTGGCT GATTTTGCGG TTGAACAAGA AGTAACAGCT    4800
GGAGACCGTG TTGTGGTTAT CGACGGTCTG GACCGCATGG CTCACTTCAA AGACGATTTG    4860
GTGCTGGTTC CTTTGACCAC CAAAGTAGTA GGCGGTTCTA GGTGCACCAT TTGTGACGTC    4920
GTTAAGGAAG AAGCCAATGA CACCCCAGTT AAGCCAATGC CAGCAGGAG ACGCCGCAAG     4980
GGCCTGCCTA AAGGTGCTCA GTTGGAGTGG ACCGTCACC AGGAAGAGAA GAGGAACGCC     5040
GGTGATGATG ATTTTGCGGT CTCGAATGAT TATGTCAAGA GAGTGCCAAA GTACTGGGAT    5100
```

-continued

```
CCCAGCGACA CCCGAGGCAC GACAGTGAAA ATCGCCGGCA CTACCTATCA GAAAGTGGTT    5160

GACTATTCAG GCAATGTGCA TTACGTGGAG CATCAGGAAG ATCTGCTAGA CTACGTGCTG    5220

GGCAAGGGGA GCTATGAAGG CCTAGATCAG GACAAAGTGT TGGACCTCAC AAACATGCTT    5280

AAAGTGGACC CCACGGAGCT CTCCTCCAAA GACAAAGCCA AGGCGCGTCA CGTTGCTCAT    5340

CTGCTGTTGG ATCTGGCTAA CCCAGTTGAG GCAGTGAATC AGTTAAACTG AGAGCGCCCC    5400

ACATCTTTCC CGGCGATGTG GGGCGTCGGA CCTTTGCTGA CTCTAAAGAC AAGGGTTTCG    5460

TGGCTCTACA CAGTCGCACA ATGTTTTTAG CTGCCCGGGA CTTTTTATTT AACATCAAAT    5520

TTGTGTGCGA CGAAGAGTTC ACAAAGACCC CAAAAGACAC ACTGCTTGGG TACGTACGCG    5580

CCTGCCCTGG TTACTGGTTT ATTTTCCGTC GTACGCACCG GTCGCTGATT GATGCATACT    5640

GGGACAGTAT GGAGTGCGTT TACGCGCTTC CCACCATATC TGATTTTGAT GTGAGCCCAG    5700

GTGACGTCGC AGTGACGGGC GAGCGATGGG ATTTTGAATC TCCCGGAGGA GGCCGTGCAA    5760

AACGTCTCAC AGCTGATCTG GTGCACGCTT TTCAAGGGTT CCACGGAGCC TCTTATTCCT    5820

ATGATGACAA GGTGGCAGCT GCTGTCAGTG GTGACCCGTA TCGGTCGGAC GGCGTCTTGT    5880

ATAACACCCG TTGGGGCAAC ATTCCATATT CTGTCCCAAC CAATGCTTTG GAAGCCACAG    5940

CTTGCTACCG TGCTGGATGT GAGGCCGTTA CCGACGGGAC CAACGTCATC GCAACAATTG    6000

GGCCCTTCCC GGAGCAACAA CCCATACCGG ACATCCCAAA GAGCGTGCTT GACAACTGCG    6060

CTGACATCAG CTGTGACGCT TTCATAGCGC CCGCTGCAGA GACAGCCCTG TGTGGAGATT    6120

TAGAGAAATA CAACCTATCC ACGCAGGGTT TTGTGTTGCC TAGTGTTTTC TCCATGGTGC    6180

GGGCGTACTT AAAAGAGGAG ATTGGAGACG CTCCACCACT CTACTTGCCA TCTACTGTAC    6240

CATCTAAAAA TTCACAAGCC GGAATTAACG GCGCTGAGTT TCCTACAAAG TCTTTACAGA    6300

GCTACTGTTT GATTGATGAC ATGGTGTCAC AGTCCATGAA AAGCAATCTA CAAACCGCCA    6360

CCATGGCGAC TTGTAAACGG CAATACTGTT CCAAATACAA GATTAGGAGC ATTCTGGGCA    6420

CCAACAATTA CATTGGCCTA GGTTTGCGTG CCTGCCTTTC GGGGGTTACG GCCGCATTCC    6480

AAAAAGCTGG AAAGGATGGG TCACCGATTT ATTTGGGCAA GTCAAAATTC GACCCGATAC    6540

CAGCTCCTGA CAAGTACTGC CTTGAAACAG ACCTGGAGAG TTGTGATCGC TCCACCCCGG    6600

CTTTGGTGCG TTGGTTCGCT ACTAATCTTA TTTTTGAGCT AGCTGGCCAG CCCGAGTTGG    6660

TGCACAGCTA CGTGTTGAAT TGCTGTCACG ATCTAGTTGT GGCGGGTAGT GTAGCATTCA    6720

CCAAACGCGG GGGTTTGTCA TCTGGAGACC CTATACTTTC CATTTCCAAT ACCATCTATT    6780

CATTGGTGCT GTACACCCAG CACATGTTGC TATGTGGACT TGAAGGCTAT TTCCCAGAGA    6840

TTGCAGAAAA ATATCTTGAT GGCAGCCTGG AGCTGCGGGA CATGTTCAAG TACGTTCGAG    6900

TGTACATCTA CTCGGACGAT GTGGTTCTAA CCACACCCAA CCAGCATTAC GCGGCCAGCT    6960

TTGACCGCTG GTCCCCCAC CTGCAGGCGC TGCTAGGTTT CAAGGTTGAC CCAAAGAAAA    7020

CTGTGAACAC CAGCTCCCCT TCCTTTTTGG GCTGCCGGTT CAAGCAAGTG ACGGCAAGT    7080

GTTATCTAGC CAGTCTTCAG GACCGCGTTA CACGCTCTCT GTTATACCAC ATTGGTGCAA    7140

AGAATCCCTC AGAGTACTAT GAAGCTGCTG TTTCCATCTT TAAGGACTCC ATTATCTGCT    7200

GTGATGAAGA CTGGTGGACG GACCTCCATC GACGTATCAG TGGCGCTGCG CGTACCGACG    7260

GAGTTGAGTT CCCCACCATT GAAATGTTAA CATCCTTCCG CACCAAGCAG TATGAGAGTG    7320

CCGTGTGCAC AGTTTGTGGG GCCGCCCCCG TGGCCAAGTC TGCTTGTGGA GGGTGGTTCT    7380

GTGGCAATTG TGTCCCGTAC CACGCGGGTC ATTGTCACAC AACCTCGCTC TTCGCCAACT    7440

GCGGGCACGA CATCATGTAC CGCTCCACTT ACTGCACAAT GTGTGAGGGT TCCCCAAAAC    7500
```

-continued

```
AGATGGTACC AAAAGTGCCT CACCCGATCC TGGATCATTT GCTGTGCCAC ATTGATTACG    7560

GCAGTAAAGA GGAACTAACT CTGGTAGTGG CGGATGGTCG AACAACATCA CCGCCCGGGC    7620

GCTACAAAGT GGGTCACAAG GTAGTCGCCG TGGTTGCAGA TGTGGGAGGC AACATTGTGT    7680

TTGGGTGCGG TCCTGGATCA CACATCGCAG TACCACTTCA GGATACGCTC AAGGGCGTGG    7740

TGGTGAATAA AGCTCTGAAG AACGCCGCCG CCTCTGAGTA CGTGGAAGGA CCCCCTGGGA    7800

GTGGGAAGAC TTTTCACCTG GTCAAAGATG TGCTAGCCGT GGTCGGTAGC GCGACCTTGG    7860

TTGTGCCCAC CCACGCGTCC ATGCTGGACT GCATCAACAA GCTCAAACAA GCGGGCGCCG    7920

ATCCATACTT TGTGGTGCCC AAGTATACAG TTCTTGACTT TCCCCGGCCT GGCAGTGGAA    7980

ACATCACAGT GCGACTGCCA CAGGTCGGAA CCAGTGAGGG AGAAACCTTT GTGGATGAGG    8040

TGGCCTACTT CTCACCAGTG GATCTGGCGC GCATTTTAAC CCAGGGTCGA GTCAAGGGTT    8100

ACGGTGATTT AAATCAGCTC GGGTGCGTCG GACCCGCGAG CGTGCCACGT AACCTTTGGC    8160

TCCGACATTT TGTCAGCCTG GAGCCCTTGC GAGTGTGCCA TCGATTCGGC GCTGCTGTGT    8220

GTGATTTGAT CAAGGGCATT TATCCTTATT ATGAGCCAGC TCCACATACC ACTAAAGTGG    8280

TGTTTGTGCC AAATCCAGAC TTTGAGAAAG GTGTAGTCAT CACCGCCTAC CACAAAGATC    8340

GCGGTCTTGG TCACCGCACA ATTGATTCAA TTCAAGGCTG TACATTCCCT GTTGTGACTC    8400

TTCGACTGCC CACACCCCAA TCACTGACGC GCCCGCGCGC AGTTGTGGCG GTTACTAGGG    8460

CGTCTCAGGA ATTATACATC TACGACCCCT TTGATCAGCT TAGCGGGTTG TTGAAGTTCA    8520

CCAAGGAAGC AGAGGCGCAG GACTTGATCC ATGGCCCACC TACAGCATGC CACCTGGGCC    8580

AAGAAATTGA CCTTTGGTCC AATGAGGGCC TCGAATATTA CAAGGAAGTC AACCTGCTGT    8640

ACACACACGT CCCCATCAAG GATGGTGTAA TACACAGTTA CCCTAATTGT GGCCCTGCCT    8700

GTGGCTGGGA AAAGCAATCC AACAAAATTT CGTGCCTCCC GAGAGTGGCA CAAAATTTGG    8760

GCTACCACTA TTCCCCAGAC TTACCAGGAT TTTGCCCCAT ACCAAAAGAA CTCGCTGAGC    8820

ATTGGCCCGT AGTGTCCAAT GATAGATACC CGAATTGCTT GCAAATTACC TTACAGCAAG    8880

TATGTGAACT CAGTAAACCG TGCTCAGCGG GCTATATGGT TGGACAATCT GTTTTCGTGC    8940

AGACGCCTGG TGTGACATCT TACTGGCTTA CTGAATGGGT CGACGGCAAA GCGCGTGCTC    9000

TACCAGATTC CTTATTCTCG TCCGGTAGGT TCGAGACTAA CAGCCGCGCT TTCCTCGATG    9060

AAGCCGAGGA AAAGTTTGCC GCCGCTCACC CTCATGCCTG TTTGGGAGAA ATTAATAAGT    9120

CCACCGTGGG AGGATCCCAC TTCATCTTTT CCCAATATTT ACCACCATTG CTACCCGCAG    9180

ACGCTGTTGC CCTGGTAGGT GCTTCATTGG CTGGGAAAGC TGCTAAAGCT GCTTGCAGCG    9240

TTGTTGATGT CTATGCTCCA TCATTTGAAC CTTATCTACA CCCTGAGACA CTGAGTCGCG    9300

TGTACAAGAT TATGATCGAT TTCAAGCCGT GTAGGCTTAT GGTGTGGAGA AACGCGACCT    9360

TTTATGTCCA AGAGGGTGTT GATGCAGTTA CATCAGCACT AGCAGCTGTG TCCAAACTCA    9420

TCAAAGTGCC GGCCAATGAG CCTGTTTCAT TCCATGTGGC ATCAGGGTAC AGAACCAACG    9480

CGCTGGTAGC GCCCCAGGCT AAAATTTCAA TTGGAGCCTA CGCCGCCGAG TGGGCACTGT    9540

CAACTGAACC GCCACCTGCT GGTTATGCGA TCGTGCGGCG ATATATTGTA AAGAGGCTCC    9600

TCAGCTCAAC AGAAGTGTTC TTGTGCCGCA GGGGTGTTGT GTCTTCCACC TCAGTGCAGA    9660

CCATTTGTGC ACTAGAGGGA TGTAAACCTC TGTTCAACTT CTTACAAATT GGTTCAGTCA    9720

TTGGGCCCGT GTGATGGGCT TAGTGTGGTC ACTGATTTCA AATTCTATTC AGACTATTAT    9780

TGCTGATTTT GCTATTTCTG TGATTGATGC AGCGCTTTTC TTTCTCATGC TACTTGCATT    9840
```

```
GGCTGTTGTT ACTGTGTTTC TTTTCTGGCT CATTGTTGCC ATCGGCCGCA GCTTGGTGGC   9900

GCGGTGTTCA CGAGGTGCGC GTTACAGACC TGTTTAAGGA TTTGCAGTGC ACAACCTGC    9960

GCGCGAAAGA TGCCTTCCCG AGTCTGGGAT ATGCTCTGTC GATTGGCCAG TCGAGGCTAT  10020

CGTATATGCT GCAGGATTGG TTGCTTGCTG CGCACCGCAA GGAAGTTATG CCTTCCAATA  10080

TCATGCCTAT GCCCGGTCTT ACTCCTGATT GCTTTGACCA TCTGGAGTCT TCTAGCTATG  10140

CTCCATTTAT CAATGCCTAT CGGCAGGCAA TTTTGAGTCA ATACCCACAA GAGCTCCAGC  10200

TCGAAGCCAT CAACTGTAAA TTGCTTGCTG TGGTTGCACC GGCATTGTAT CATAATTACC  10260

ATCTAGCCAA TTTGACCGGA CCGGCCACAT GGGTCGTGCC TACAGTGGGC CAGTTGCACT  10320

ATTATGCTTC TTCCTCTATT TTTGCTTCAT CTGTGGAAGT GTTGGCAGCA ATAATACTAC  10380

TATTTGCATG CATACCACTA GTGACACGAG TGTACATCTC TTTTACGCGG CTAATGTCAC  10440

CTTCCCGTCG CACTTCCAGC GGCACTTTGC CGCGGCGCAA GATTTTGTAG TGCACACGGG  10500

TTATGAATAT GCCGGGTCA CTATGTTAGT GCACTTGTTT GCCAACTTGG TTCTGACATT    10560

TCCGAGCTTA GTTAATTGTT CCCGCCCTGT GAATGTCTTT GCTAATGCTT CTTGCGTGCA  10620

AGTGGTTTGT AGTCATACCA ACTCAACTAC TGGCTTGGGT CAACTTTCTT TTTCCTTTGT  10680

AGATGAAGAT CTACGGCTGC ATATCAGGCC TACTCTTATT TGTTGGTTTG CCTTGTTGTT  10740

GGTGCACTTT CTACCCATGC CACGCTGCAG AGGCTCGTAA TTTTACTTAC ATTAGTCATG  10800

GATTGGGCCA CGTGCACGGT CATGAGGGGT GTAGGAATTT TATTAATGTC ACTCATTCTG  10860

CATTTCTTTA TCTTAATCCC ACCACTCCCA CTGCGCCGGC TATAACTCAT TGTTTACTTC  10920

TGGTTCTGGC AGCCAAAATG GAACACCCAA ACGTACTAT CTGGCTGCAG CTGCAGCCGT    10980

TTGGGTATCA TGTGGCTGGC GATGTCATTG TCAACTTGGA AGAGGACAAG AGGCATCCTT  11040

ACTTTAAACT TTTGAGAGCG CCGGCTTTAC CGCTTGGTTT TGTGGCTATA GTTTATGTTC  11100

TTTTACGACT GGTACGTTGG GCTCAACG ATG TTA TCT ATG ATT GTA TTG CTA     11152
                               Met Leu Ser Met Ile Val Leu Leu
                                1               5

TTC TTG CTT TGG GGT GCG CCA TCA CAT GCT TAC TTC TCA TAC TAC ACC    11200
Phe Leu Leu Trp Gly Ala Pro Ser His Ala Tyr Phe Ser Tyr Tyr Thr
    10              15                  20

GCT CAG CGC TTC ACA GAC TTC ACC TTG TGT ATG CTG ACG GAT CGC GGC    11248
Ala Gln Arg Phe Thr Asp Phe Thr Leu Cys Met Leu Thr Asp Arg Gly
25                  30                  35                  40

GTT ATT GCC AAT TTG CTG CGA TAT GAT GAG CAC ACT GCT TTG TAC AAT    11296
Val Ile Ala Asn Leu Leu Arg Tyr Asp Glu His Thr Ala Leu Tyr Asn
            45                  50                  55

TGT TCC GCC AGT AAA ACC TGT TGG TAT TGC ACA TTC CTG GAC GAA CAG    11344
Cys Ser Ala Ser Lys Thr Cys Trp Tyr Cys Thr Phe Leu Asp Glu Gln
                60                  65                  70

ATT ATC ACG TTT GGA ACC GAT TGT GAT GAC ACC TAC GCG GTC CCA GTT    11392
Ile Ile Thr Phe Gly Thr Asp Cys Asp Asp Thr Tyr Ala Val Pro Val
        75                  80                  85

GCT GAG GTC CTG GAA CAG GCG CAT GGA CCG TAC AGT GCG CTG TTT GAT    11440
Ala Glu Val Leu Glu Gln Ala His Gly Pro Tyr Ser Ala Leu Phe Asp
    90                  95                  100

GAC ATG CCC CCT TTT ATT TAC TAT GGC CGT GAA TTC GGC ATA GTT GTG    11488
Asp Met Pro Pro Phe Ile Tyr Tyr Gly Arg Glu Phe Gly Ile Val Val
105                 110                 115                 120

TTG GAT GTG TTT ATG TTC TAT CCC GTT TTA GTT CTG TTT TTC TTA TCA    11536
Leu Asp Val Phe Met Phe Tyr Pro Val Leu Val Leu Phe Phe Leu Ser
                125                 130                 135

GTA CTACCCTATG CTACGCTTAT TCTTGAAATG TGTGTATCTA TTCTGTTTAT          11589
```

```
Val

AATCTATGGC ATTTACAGCG GGGCCTACTT GGCCATGGGC ATATTTGCGG CCACGCTTGC    11649

TATACATTCA ATTGTGGTCC TCCGCCAATT ACTGTGGTTA TGCCTGGCTT GGCGATACCG    11709

CTGTACGCTT CACGCGTCCT TTATATCAGC TGAGGGAAA GTGTACCCCG TAGACCCCGG    11769

ACTCCCGGTT GCCGCCGTGG GCAATCGGTT GTTAGTCCCA GGTAGGCCCA CTATCGATTA    11829

TGCAGTGGCC TACGGCAGCA AAGTCAACCT TGTGAGGTTG GGGGCAGCTG AGGTATGGGA    11889

GCCATAGATT CATTTTGTGG TGACGGGATT TTAGGTGAGT ATCTAGATTA CTTTATTCTG    11949

TCCGTCCCAC TCTTGCTGTT GCTTACTAGG TATGTAGCAT CTGGGTTAGT GTATGTTTTG    12009

ACTGCCTTGT TCTATTCCTT TGTATTAGCA GCTTATATTT GGTTTGTTAT AGTTGGAAGA    12069

GCCTTTTCTA CTGCTTATGC TTTTGTGCTT TTGGCTGCTT TTCTGTTATT AGTAATGAGG    12129

ATGATTGTGG GTATGATGCC TCGTCTTCGG TCCATTTTCA ACCATCGCCA ACTGGTGGTA    12189

GCTGATTTTG TGGACACACC TAGTGGACCT GTTCCCATCC CCCGCTCAAC TACTCAGGTA    12249

GTGGTTCGCG GCAACGGGTA CACCGCAGTT GGTAACAAGC TTGTCGATGG CGTCAAGACG    12309

ATCACGTCCG CAGGCCGCCT CTTTTCGAAA CGGACGGCGG CGACAGCCTA CAAGCTACAA    12369

TGACCTACTG CGCATGTTTG GTCAGATGCG GGTCCGCAAA CCGCCCGCGC AACCCACTCA    12429

GGCTATTATT GCAGAGCCTG GAGACCTTAG GCATGATTTA AATCAACAGG AGCGCGCCAC    12489

CCTTTCGTCG AACGTACAAC GGTTCTTCAT GATTGGGCAT GGTTCACTCA CTGCAGATGC    12549

CGGAGGACTC ACGTACACCG TCAGTTGGGT TCCTACCAAA CAAATCCAGC GCAAAGTTGC    12609

GCCTCCAGCA GGGCCGTAAG ACGTGGATAT TCTCCTGTGT GGCGTCATGT TGAAGTAGTT    12669

ATTAGCCACC CAGGAACC                                                  12687
```

(2) INFORMATION FOR SEQ ID NO: 2:

(i) SEQUENCE CHARACTERISTICS:
        (A) LENGTH: 137 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Leu Ser Met Ile Val Leu Leu Phe Leu Leu Trp Gly Ala Pro Ser
 1               5                  10                  15

His Ala Tyr Phe Ser Tyr Tyr Thr Ala Gln Arg Phe Thr Asp Phe Thr
            20                  25                  30

Leu Cys Met Leu Thr Asp Arg Gly Val Ile Ala Asn Leu Leu Arg Tyr
        35                  40                  45

Asp Glu His Thr Ala Leu Tyr Asn Cys Ser Ala Ser Lys Thr Cys Trp
    50                  55                  60

Tyr Cys Thr Phe Leu Asp Glu Gln Ile Ile Thr Phe Gly Thr Asp Cys
65                  70                  75                  80

Asp Asp Thr Tyr Ala Val Pro Val Ala Glu Val Leu Glu Gln Ala His
                85                  90                  95

Gly Pro Tyr Ser Ala Leu Phe Asp Asp Met Pro Pro Phe Ile Tyr Tyr
            100                 105                 110

Gly Arg Glu Phe Gly Ile Val Val Leu Asp Val Phe Met Phe Tyr Pro
        115                 120                 125

Val Leu Val Leu Phe Phe Leu Ser Val
    130                 135
```

(2) INFORMATION FOR SEQ ID NO: 3:

(i) SEQUENCE CHARACTERISTICS:
        (A) LENGTH: 119 amino acids
        (B) TYPE: amino acid
        (D) TOPOLOGY: unknown (ii) MOLECULE TYPE: peptide (xi) SEQUENCE DESCRIPTION: SEQ ID NO: 3:

```
Tyr Phe Ser Tyr Tyr Thr Ala Gln Arg Phe Thr Asp Phe Thr Leu Cys
1               5                   10                  15

Met Leu Thr Asp Arg Gly Val Ile Ala Asn Leu Leu Arg Tyr Asp Glu
            20                  25                  30

His Thr Ala Leu Tyr Asn Cys Ser Ala Ser Lys Thr Cys Trp Tyr Cys
        35                  40                  45

Thr Phe Leu Asp Glu Gln Ile Ile Thr Phe Gly Thr Asp Cys Asp Asp
    50                  55                  60

Thr Tyr Ala Val Pro Val Ala Glu Val Leu Glu Gln Ala His Gly Pro
65                  70                  75                  80

Tyr Ser Ala Leu Phe Asp Asp Met Pro Pro Phe Ile Tyr Tyr Gly Arg
                85                  90                  95

Glu Phe Gly Ile Val Val Leu Asp Val Phe Met Phe Tyr Pro Val Leu
                100                 105                 110

Val Leu Phe Phe Leu Ser Val
            115
```

(2) INFORMATION FOR SEQ ID NO: 4:

(i) SEQUENCE CHARACTERISTICS:
        (A) LENGTH: 110 amino acids
        (B) TYPE: amino acid
        (D) TOPOLOGY: unknown (ii) MOLECULE TYPE: peptide (xi) SEQUENCE DESCRIPTION: SEQ ID NO: 4:

```
Phe Thr Asp Phe Thr Leu Cys Met Leu Thr Asp Arg Gly Val Ile Ala
1               5                   10                  15

Asn Leu Leu Arg Tyr Asp Glu His Thr Ala Leu Tyr Asn Cys Ser Ala
            20                  25                  30

Ser Lys Thr Cys Trp Tyr Cys Thr Phe Leu Asp Glu Gln Ile Ile Thr
        35                  40                  45

Phe Gly Thr Asp Cys Asp Asp Thr Tyr Ala Val Pro Val Ala Glu Val
    50                  55                  60

Leu Glu Gln Ala His Gly Pro Tyr Ser Ala Leu Phe Asp Asp Met Pro
65                  70                  75                  80

Pro Phe Ile Tyr Tyr Gly Arg Glu Phe Gly Ile Val Val Leu Asp Val
                85                  90                  95

Phe Met Phe Tyr Pro Val Leu Val Leu Phe Phe Leu Ser Val
                100                 105                 110
```

(2) INFORMATION FOR SEQ ID NO: 5:

(i) SEQUENCE CHARACTERISTICS:
        (A) LENGTH: 23 amino acids
        (B) TYPE: amino acid
        (D) TOPOLOGY: unknown (ii) MOLECULE TYPE: peptide

```
      (xi) SEQUENCE DESCRIPTION: SEQ ID NO: 5:

Thr Phe Gly Thr Asp Cys Asp Asp Thr Tyr Ala Val Pro Val Ala Glu
1               5                   10                  15

Val Leu Glu Gln Ala His Gly
            20

(2) INFORMATION FOR SEQ ID NO: 6:

(i) SEQUENCE CHARACTERISTICS:
         (A) LENGTH: 44 amino acids
         (B) TYPE: amino acid
         (D) TOPOLOGY: unknown (ii) MOLECULE TYPE: peptide (xi) SEQUENCE DESCRIPTION: SEQ ID NO: 6:

Tyr Asn Cys Ser Ala Ser Lys Thr Cys Trp Tyr Cys Thr Phe Leu Asp
1               5                   10                  15

Glu Gln Ile Ile Thr Phe Gly Thr Asp Cys Asp Asp Thr Tyr Ala Val
            20                  25                  30

Pro Val Ala Glu Val Leu Glu Gln Ala His Gly Pro
            35                  40

(2) INFORMATION FOR SEQ ID NO: 7:

(i) SEQUENCE CHARACTERISTICS:
         (A) LENGTH: 13 amino acids
         (B) TYPE: amino acid
         (D) TOPOLOGY: unknown (ii) MOLECULE TYPE: peptide (xi) SEQUENCE DESCRIPTION: SEQ ID NO: 7:

Ala Val Pro Val Ala Glu Val Leu Glu Gln Ala His Gly
1               5                   10
```